United States Patent [19]

Young et al.

[11] 4,231,973

[45] Nov. 4, 1980

[54] NEBULIZER WITH VARIABLE FLOW RATE CONTROL AND ASSOCIATED METHOD

[75] Inventors: Joe W. Young, Torrance; Charles Odenthal, Upland, both of Calif.

[73] Assignee: C. R. Bard, Inc., Murray Hill, N.J.

[21] Appl. No.: 947,109

[22] Filed: Sep. 29, 1978

[51] Int. Cl.³ .................. A61M 11/02; B01F 3/04
[52] U.S. Cl. .................. 261/78 A; 128/200.11; 128/200.21; 239/338; 239/370; 261/DIG. 65
[58] Field of Search .... 261/78 A, DIG. 65, DIG. 47; 239/120, 338, 370; 128/193, 194

[56] References Cited

U.S. PATENT DOCUMENTS

| 2,342,602 | 2/1944 | Reitz, Jr. ............. 261/DIG. 47 |
| 2,605,089 | 7/1952 | Dautrebande ............. 261/78 A |
| 2,882,026 | 4/1959 | Eichelman ............. 261/78 A X |
| 3,339,901 | 9/1967 | Walker ............. 261/DIG. 47 |
| 3,874,379 | 4/1975 | Enfield et al. ............. 261/DIG. 65 |
| 3,913,843 | 10/1975 | Cambio, Jr. ............. 261/78 A X |
| 4,007,238 | 2/1977 | Glenn ............. 261/78 A |
| 4,045,525 | 8/1977 | Huggins ............. 261/DIG. 65 |

*Primary Examiner*—Richard L. Chiesa
*Attorney, Agent, or Firm*—Richard H. Zaitlen

[57] ABSTRACT

A nebulizer device for use in a breathing circuit is disclosed. The device consists of a nebulization chamber in flow communication with a gas inlet and a gas outlet. The gas inlet is configured to be coupled to a source of gas which is directed into the nebulization chamber. The gas outlet is configured to direct gas from the chamber to a patient connection. A uniquely configured siphon jet assembly for producing fine particles of liquid extends into the nebulization chamber and is movable into a plurality of positions. This permits the regulation of both the amount of liquid entrained by the gas as well as the size of the liquid particles formed.

11 Claims, 3 Drawing Figures

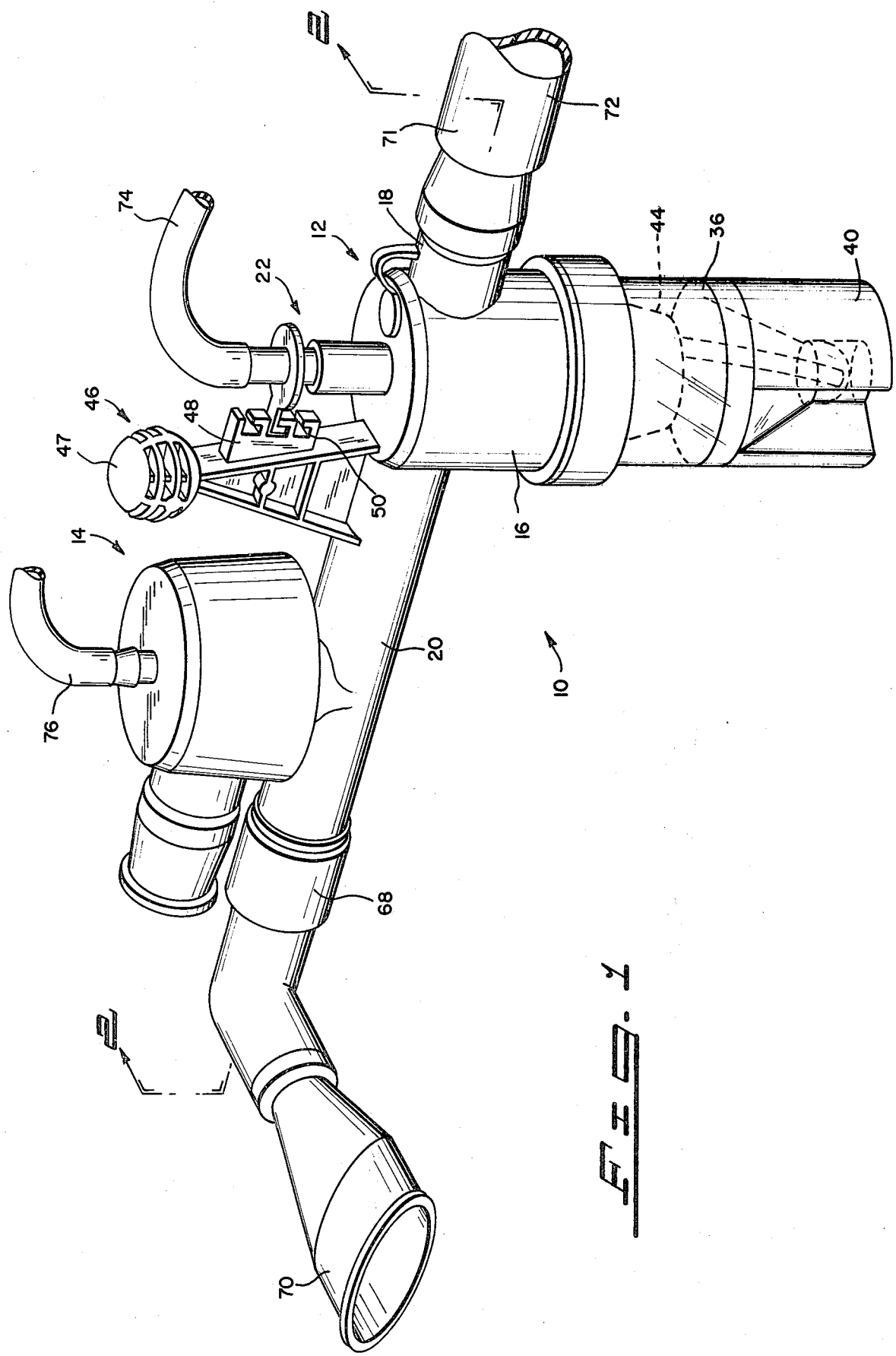

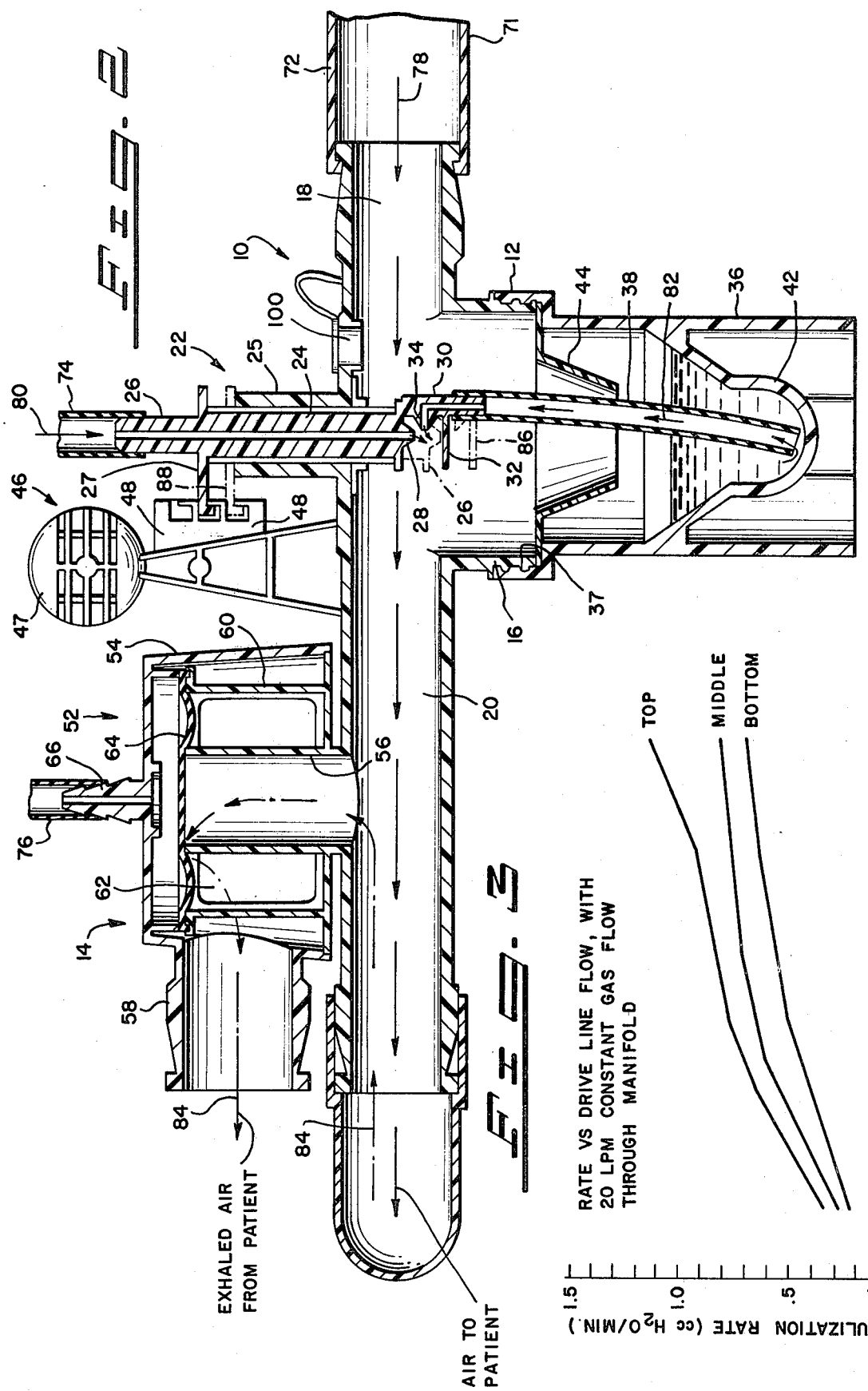

NEBULIZER WITH VARIABLE FLOW RATE CONTROL AND ASSOCIATED METHOD

BACKGROUND OF THE INVENTION

1. Field of the Invention

This invention relates to inhalation therapy devices, and more particularly, to the design and construction of a nebulizer which has a variable flow rate control.

2. Prior Art

It has been determined that a number of respiratory ailments can be treated by the inhalation of finely divided particles of water or other liquid medicaments. However, in the case of some ailments, the particles must travel into the lower respiratory tract. In other ailments, application of the particles to the upper respiratory tract is preferred. In either situation, it is also desirable to be able to regulate the rate at which the liquid medicament is supplied per unit time. This is generally referred to as the "nebulization rate". By regulating both the nebulization rate and the particle size, accurate treatment of a wide range of respiratory diseases can be achieved.

The prior art is well aware of using of finely divided liquid particles in the treatment of respiratory ailments, and a number of prior art nebulizer devices have evolved. In general, these type of devices are shown in U.S. Pat. Nos. 2,882,026; 3,874,379; and 4,007,238. These nebulizers introduce a stream of gas into a chamber which entrains liquid particles. The liquid particles in the gas stream are then directed to the patient. Such devices contain a number of shortcomings. For example, they are constructed such that for a given flow rate of gas (LPM) into the chamber, liquid particles of a specific size are produced. In addition, the number of particles entrained by the gas per unit time is also fixed for any given flow rate of gas. If one were to change the flow rate of gas through these prior art devices, it is believed that not only would the amount of liquid particles entrained by the gas be changed, but the size of the liquid particles would also be changed. Thus, merely changing the flow rate of gas may prevent the particles from being directed either to the upper or lower respiratory tract.

U.S. Pat. No. 2,882,026 does disclose the use of a rotatable nozzle to produce ultra small liquid particles. This nozzle is mounted on a tube which is secured in place by means of a sleeve nut. However, such device requires that the nozzle be fixed in one position prior to operation of the device. In addition, such limited movement is not believed to be sufficient to achieve the necessary regulation of both the particle size and nebulization rate.

SUMMARY OF THE INVENTION

It is an object of this invention to provide an inexpensive single-patient nebulizer device for use in IPPB therapy which includes a simple, easy to use means of controlling the nebulization rate as well as the size of the liquid particles produced. The device of the present invention thus permits tailoring of the inhalation therapy to the individual patient's needs. In general, the nebulizer device of the present invention is designed for use in a gas flow circuitry such as an IPPB circuit and includes a nebulizer section having a chamber in flow communication with a gas inlet tube and a gas outlet tube. The gas inlet tube is configured to be coupled to a source of gas such that the gas is directed into a nebulization chamber. The gas outlet tube is configured to direct the gas from the nebulization chamber to a patient connection.

A siphon jet assembly having an elongated tubular member extends into the chamber. The elongated tubular member has an inlet port adjacent one end thereof exterior to the chamber configured to be joined to a second source of gas. A first nozzle is disposed on the siphon jet assembly adjacent the other end thereof. This first nozzle is configured to direct the gas from a second source into the chamber so as to form a gas jet spray therein. A downwardly extending section is joined to the siphon jet assembly and has an outwardly extending impact post disposed opposite the first nozzle. The siphon jet assembly is vertically movable and rotatable in the chamber such that the first nozzle and the impact post can be moved into a plurality of predetermined vertical positions. The provision for movement of the siphon jet assembly represents one advancement of the present invention over the prior art. In this manner, the amount of medicated gas (i.e. the gas/liquid mixture) to the patient can be easily controlled without changing the flow rate of the gas through the device from either source of gas. Movement of the siphon jet assembly also changes the size of the liquid particles formed in the chamber and then entrained as hereinafter described.

A vial for water or other liquid medication is also joined to the chamber and supplies the chamber with the liquid. A liquid supply conduit is joined to the downwardly extending section on the siphon jet assembly and extends into the liquid in the vial. The liquid supply conduit is joined to the downward extending section such that when gas from the second source flows through the first nozzle and into the chamber, liquid in the vial is caused to travel through the liquid supply conduit and into the chamber adjacent the first nozzle. This action is caused by the venturi effect created by the jet action of the first nozzle adjacent a port on the downwardly extending section. As the liquid from the vial travels into the chamber, it is entrained by the jet spray from the first nozzle and is directed against the impact post. As the liquid impinges upon the impact post, the liquid is dispersed into fine particles. The dispersion of fine liquid particles thus created is entrained in the gas from the first source as it travels through the chamber.

As the patient inhales, the now-medicated gas flows through the outlet tube also coupled to the chamber, and, ultimately, to the patient. Upon exhalation, the exhaled gas flows back through the outlet tube and through an exhaust section. The exhaust section is also in flow communication with the gas outlet tube and controls the exhalation of the gas exhaled by the patient. Preferably, the exhaust section is directly joined to the nebulizer device and forms a complete manifold apparatus. However, the nebulizer device can be made in which it is separate and discrete from the exhaust section.

Because the siphon jet assembly is movable in the chamber, one can selectively regulate the amount of liquid entrained by the gas as it flows through the chamber to the patient without varying the flow rate of the gas. In addition to regulating the amount of liquid entrained by the gas, movement of the siphon jet assembly in the chamber also regulates the particle size. In this manner, smaller particles can be produced which have been found to be better in the treatment of lower respiratory tract ailments. Larger particles can also be produced which have been found to be better in the treatment of upper respiratory tract ailments.

The novel features which are believed to be characteristic of the invention, both as to its organization and method of operation, together with further objectives and advantages thereof, will be better understood from the following description considered in connection with the accompanying drawings in which a presently preferred embodiment of the invention is illustrated by way of example. It is to be expressly understood, however, that the drawings are for the purpose of illustration and description only, and are not intended as a definition of the limits of the invention.

BRIEF DESCRIPTION OF THE DRAWINGS

FIG. 1 is a perspective view of the nebulizer device of the present invention;

FIG. 2 is a cross-sectional view taken along lines 2—2 of FIG. 1 and showing the internal aspects of the nebulizer device of the present invention.

FIG. 3 is a graph showing the relative nebulization rates produced by the various positions of the siphon jet assembly at a constant gas flow rate into the device.

DETAILED DESCRIPTION OF THE INVENTION

The Device

Referring first to FIGS. 1 and 2, one can see the manifold 10 of the present invention. The manifold 10 comprises a nebulizer section 12 and an exhaust section 14. The nebulizer section 12 has a nebulization chamber 16 of a generally cylindrical configuration. A gas inlet tube or conduit 18 extends into the chamber 16 from one side thereof, and a gas outlet tube or conduit 20 extends from the chamber 16 on the other side thereof. In the preferred embodiment, the gas inlet 18 and the gas outlet 20 are in substantial axial alignment, i.e. an in-line configuration with the nebulizer chamber 16 depending therefrom. The nebulizer section 12 also includes a uniquely designed siphon jet assembly 22. The siphon jet assembly 22 extends into the chamber 16 from the top thereof and is vertically movable therein. The siphon jet assembly 22 is comprised of a tubular member 24 which extends through a sleeve 25 located on the chamber 16. Tubular member 24 is axially rotatable in sleeve member 25. Adjacent the top 26 of the siphon jet assembly 22 is an outwardly extending flange member 27. Disposed at the other end of the siphon jet assembly 22 is a first nozzle 28. Nozzle 28 is configured to produce a high velocity gas jet stream in the chamber 16. A downwardly extending section 30 is coupled to the siphon jet assembly 22 adjacent the first nozzle 28 and is also of tubular construction. Section 30 has an outwardly extending impact post 32 and a second nozzle 34. Impact post 32 and nozzle 34 are disposed on section 30 so as to be adjacent the first nozzle 28.

Referring specifically to FIG. 2, one can see that impact post 32 extends outwardly from section 30 so as to be generally perpendicular to the first nozzle 28. Nozzle 34 is also located on section 30 so as to be generally perpendicular to nozzle 28 such that a gas jet from nozzle 28 flows across nozzle 34. In this manner, a venturi effect is created. Hence, siphon jet assembly 22 acts as the venturi means for supplying liquid particles to the gas flowing through chamber 16.

A vial 36 is joined to the chamber 16 and a liquid supply conduit 38 extends into the vial 36. Conduit 38 is also joined to the downwardly extending section 30 so as to be in flow communication with the second nozzle 34. The vial 36 has a shaped base section 40 which is circumferentially disposed about a bottom section of the vial 36. In the preferred embodiment, the vial 36 includes a generally frusto-conical section 42 with a spherical bottom, and is adapted to contain any of the well known medicaments to be supplied to the respiratory tract as hereinafter described. A funnel member 44 is preferably placed atop the vial 36 and is secured in position when the vial 36 is joined to the chamber 16. Funnel member 44 helps retain the liquid in the vial 16.

A mounting member 46 is disposed on the manifold 10 such that the manifold 10 can be coupled to a mounting support as is well known in the art. The mounting member 46 includes a specifically configured mounting knob 47 in the preferred embodiment. Disposed adjacent the mounting member 46 is a uniquely configured notched member 48 which has a plurality of notches 50 formed therein. In the preferred embodiment, such member 48 has three notches 50 which selectively permit the flange member 27 to be disposed therein so as to regulate the movement of the siphon jet assembly 22 as hereinafter described. The notches 50 are configured such that flange member 27 has a secure fit therein, but one which permits member 27 to be moved without using great force. It is to be understood that other means for removably holding the siphon jet assembly 22 in a selected position are within the scope of this invention.

Again referring to FIG. 2, one can see that the exhaust section 14 includes a generally cylindrical body 52 having a cap 54 circumferentially disposed about a tubular member 56. The exhaust section 14 is in flow communication with the gas outlet conduit 20. The exhaust section 14 includes a gas outlet port 58 in flow communication with the gas outlet conduit 20. A circular member 60 circumferentially surrounds the tubular member 56 and includes a plurality of ports or windows 62. Disposed on top such circular member 60 is a flexible rubber diaphragm 64 which permits the exhaled air from the patient to exit from the manifold 10, but prevents air from traveling through exhaust section 14 to the patient through a patient connection or mouthpiece 70. Disposed on the cap 54 adjacent the top thereof is a port 66 in flow communication with the interior of the exhaust section 14. Port 66 can be joined to gas from a third source which further encourages the diaphragm 64 to remain seated on member 60 during inhalation.

Referring again to FIG. 1, one can see that a coupler member 68 is joined to the gas outlet conduit 20 and is configured to permit the manifold 10 to be joined to the mouthpiece 70. Likewise, the gas inlet conduit 18 is configured to make a good seal with flexible gas tubing 71. Before discussing the detailed aspects of the operation of the present invention, reference to FIG. 2 indicates that the siphon jet assembly 22 can be disposed into a plurality of predetermined positions. As illustrated in FIG. 2, the flange member 27 on the siphon jet assembly 22 is located in the middle notch on member 48. In this position, the first nozzle 28 is located somewhat beneath the axis 78 of the flow path of gas formed by the inlet and outlet conduits 12 and 14 respectively. Phantom lines 86 illustrate the movement of the impact post 32 as well as the first nozzle 28 when the flange member 27 is moved into the lower notch indicated by phantom lines 88. Movement of flange member 27 is easily achieved as the siphon jet assembly 22, and more specifically tubular member 24, is rotatably disposed in sleeve member 25. In the preferred embodiment, horizontal rotation of member 24 frees the flange member 27 from a given notch. Vertical movement of member 24 is then permitted which enables the first nozzle 28 and the impact post 32 to be raised and lowered in the chamber 16. In the middle and lowest notch positions, the first nozzle 28, as well as the impact post 32, are substantially below the axis 78 described hereinabove. In the top position, the nozzle 28 and the impact post 32 are located substantially along the axis 78.

Operation

In operating the manifold 10 of the present invention, a first source of gas 72 is joined to the gas inlet conduit 18, a second source of gas 74 is joined to the siphon jet assembly 22, and a third source of gas 76 is joined to the exhaust section 14. Referring now to FIG. 2, one can see that axis 78 indicates the flow path for the gas from the first source 72 through the manifold 10. Arrows 80 indicate the flow path for the gas from the second source 74 through the siphon jet assembly 22, and arrows 84 indicate the flow path of exhaled gas from the patient as it travels back through the manifold 10, through the exhaust section 14 and out of the manifold 10 through outlet port 58.

Prior to activating the manifold 10, the vial 36 is selectively removed from the chamber 16. In the preferred embodiment, vial 36 has thread members 37 which engage the chamber 16 adjacent the bottom thereof. It is to be understood that other means for joining the vial 36 to the chamber 16 are within the scope of the present invention. After the vial 36 is removed from the chamber 16, the specific medicament, which may include distilled water and the like, is poured into the vial 36. Vial 36 is preferably transparent and may include markings thereon which indicate the amount of liquid contained therein. Skirt or funnel member 44 may be removed from the vial 36 when liquid is being added, but is then replaced. Funnel member 44 is used to act as a gasket between the vial 36 and the chamber 16 and forms a substantially liquid-tight seal therebetween. Member 44 also encourages liquid back into the vial 36 as hereinafter described. Finally, member 44 also prevents liquid from flowing into the nebulizing section 12 should the manifold 10 be accidently tipped. Another method of adding medication to the vial 36 is through the removable cap 100.

After the manifold 10 is secured into position by means of mounting member 46, the various sources of gas are actuated. As the gas from the second source 74 begins to flow through the siphon jet assembly 22, fine particles of liquid are formed. More specifically, as the gas from the second source 74 flows through nozzle 28, a venturi effect is produced because gas from the second source 74 is adjacent the second nozzle member 34 on the downwardly extending section 30. Nozzle 34 is in flow communication with the liquid supply conduit 38 which extends into the vial 36. The venturi effect causes the liquid in the vial 36 to be sucked up through the liquid supply conduit 38 and to be sprayed out into the chamber 16 through nozzel 34. As the liquid in the vial 36 exits from section 30, gas from the second source 74 impinges upon it and directs it against the impact post 32. Such action causes the liquid to be broken up into fine particles or droplets so as to produce an aerosol-like mist. While the use of the impact post 32 has been found to be an effective manner of creating fine liquid particles, other means for dispersing the liquid such as balls, screens, plates and the like are also within the scope of this invention.

As the gas from the first source 72 flows through chamber 16, the liquid particles are entrained by such gas stream and are carried along conduit 20 ultimately to the patient. Particles which are too large to be entrained, flow back into the vial 36 through funnel member 44.

Upon inhalation, the patient receives the gas containing the entrained liquid particles. During exhalation, the exhaled gas is directed back through the manifold 10 so as to flow through the exhaust section 14. More specifically, as shown by arrows 84, the exhaled gas from the patient flows through tubular member 56 which is in flow communication with the gas outlet conduit 20. As the exhaled gas flows through tubular member 56, it impinges upon the diaphragm 64 which acts as a one-way valve. The exhaled gas pushes up on the diaphragm 64 and flows through the plurality of window ports 62 formed in the circular member 60. Ultimately, the gas is channeled out of the exhaust section 14 through outlet port 58. Upon inhalation, however, diaphragm 64 is disposed against the top of the tubular member 56, and thus prevents any gas from flowing through exhaust section 14 into the conduit 20. To insure that diaphragm 64 is disposed against the tubular member 56 during inhalation, gas from the third source 76 supplies positive pressure to the exhaust section 14 via port 66. This permits the cap 54 to be axially rotated to a plurality of positions so as to facilitate the convenient positioning of the outlet port 58 while maintaining the selective seal on the tubular member 56.

As discussed hereinabove, one of the problems with prior art devices was that in order to regulate the amount of medication given to a patient, that is, the amount of liquid particles which would be entrained by the gas stream supplied to the patient, the gas to the nebulizer was increased or decreased. Thus, the patient obtained a uniform amount of medication per unit time for any specific flow rate of gas. The nebulization section 12 of the present invention enables a constant LPM of gas through the nebulization chamber 16 to entrain varying amounts of liquid particles. This is achieved by selectively moving the siphon jet assembly 22 relative to the axis 78. It is understood, of course, that the specific position of the siphon jet assembly 22 in the chamber 16 is determined according to the amount of liquid particles which are to be entrained by the gas as it passes through the chamber 16.

Referring to FIG. 3, one can see a specific example which illustrates that the nebulization rate (in cc of water per minute) changes depending upon the placement of the siphon jet assembly 22 relative to the flow of gas along axis 78. It is to be understood that the specific flow rate shown in FIG. 3 is a matter of choice. FIG. 3 also illustrates that when the siphon jet assembly 22 is in the top position such that the first nozzle 28 and the impact post 32 lie along the axis 78, the nebulization rate is greater than when the nozzle 28 is lowered into the chamber 16. Axial rotation of the siphon jet assembly 22, and therefore nozzle 28, also affects the nebulization rate. It has been determined that when the nozzle 28 is rotated from its initial downstream position shown in FIG. 2, so as to face the incoming gas from the first source 72, the amount of liquid entrained increases per unit time. Thus it is also within the scope of the present invention to regulate the nebulization rate by rotation of assembly 22.

Raising and lowering the siphon jet assembly 22 also varies the size of the liquid particles entrained. As the siphon jet assembly 22 is lowered into the chamber 16, the entrained liquid particles are the smaller ones and the rate of entrained liquid particles decreases. Thus, by regulating the flow rate of the gas through the chamber 16 as well as the placement of the siphon jet assembly 22, both the size and the quantity of the liquid particles entrained can be regulated.

While a wide variety of materials, shapes and other configurations can be used in this invention, it should be understood that changes can be made without departing from the spirit or scope. For example, in the preferred embodiment all of the parts are made out of plastic materials such as nylon, PVC, acrylic resins, or the like. Of course, other materials such as reinforced plastics or even metal are within the scope of the present invention. Further, the present invention contemplates the use of heated liquids. The vial 36 may be placed in a bath such that the liquid medicament reaches a temperature either higher or lower than room-temperature. This invention, therefore, is not to be limited to the specific embodiments discussed and illustrated herein.

What is claimed is:

1. A nebulizer for supplying variable amounts of liquid to a gas flowing in a given path at a selected rate, comprising:
   conduit means having a first axis for defining said given flow path;
   a nebulization chamber intersecting said conduit means and extending away from said axis;
   venturi means for forming a movable spray of liquid particles in said flowing gas, said venturi means and spray being movable between said conduit means and said chamber relative to said axis such that the amount of liquid entrained by said flowing gas is regulated according to the displacement of the venturi means from the axis and independent of the rate of gas flow;
   liquid supply means in flow communication with said venturi means for supplying said venturi means with a liquid; and
   locking means for removably holding said venturi means in a selected location.

2. A nebulizer for supplying variable amounts of liquid according to claim 1 wherein said locking means is located outside of said nebulization chamber so as to be readily accessible.

3. A nebulizer for supplying variable amounts of liquid according to claim 1 wherein said venturi means includes a nozzle configured to direct gas from a second source into said chamber, said gas from said second source causing liquid in said liquid supply means to flow to said venturi means and to form fine particles for entrainment by said flowing gas.

4. A nebulizer for supplying particles of liquid and adapted to regulate both the amount and size of the particles, comprising:
   (a) a chamber;
   (b) a conduit having a first axis and defining an inlet and an outlet to said chamber, said inlet configured to receive gas from a first source such that said gas flows into said chamber, and said gas outlet configured to direct said gas out of said chamber;
   (c) aerosol means for forming a movable spray of fine liquid particles in said gas, said aerosol means and spray being movable between said conduit and said chamber relative to said axis into a plurality of predetermined positions such that the amount of liquid entrained by said gas varies with the position of said aerosol means and independent of the flow rate of gas; and
   (d) liquid supply means in flow communication with said aerosol means for supplying said aerosol means with a liquid.

5. A nebulizer according to claim 4 including locking means for removably holding said aerosol means in a predetermined position.

6. A nebulizer for supplying particles of liquid and adapted to regulate both the amount and size of the particles, comprising:
   (a) a chamber;
   (b) a gas flow conduit having a first axis and defining a gas inlet and a gas outlet to said chamber, said gas inlet configured to receive gas from a first source such that said gas flows into said chamber, and said gas outlet configured to direct said gas out of said chamber;
   (c) a siphon jet assembly extending into said chamber having means for receiving gas from a second source, said siphon jet assembly further having a nozzle to direct gas from said second source into said chamber, said nozzle being movable between said conduit and said chamber relative to said axis into a plurality of predetermined positions;
   (d) a vial containing a liquid joined to said chamber for supplying said siphon jet assembly with said liquid; and
   (e) a liquid supply conduit joined to said siphon jet assembly and extending into said vial such that when gas from said second source passes through said nozzle and into said chamber, liquid in said vial flows through said liquid supply conduit into said chamber and is atomized into liquid particles,
   whereby movement of said nozzle between said gas flow conduit and said chamber relative to said axis regulates the amount of liquid particles entrained by said gas flowing therethrough and the size of the liquid particles formed therein.

7. A nebulizer according to claim 6 wherein said siphon jet assembly is rotatable in said chamber.

8. A nebulizer according to claim 6 including locking means for selectively holding said first nozzle in a predetermined position relative to said axis.

9. A nebulizer according to claim 8 including a notched member, said locking member selectively engaging said notched member thereby holding said nozzle in said predetermined position.

10. A nebulizer according to claim 6 wherein said siphon jet assembly comprises an elongated tubular member extending into said chamber, said means for receiving gas from a second source disposed adjacent one end of said tubular member and said first nozzle disposed adjacent the other end thereof,
   whereby movement of said tubular member relative to said axis moves said nozzle between said gas flow conduit and said chamber.

11. A method for controlling the amount of liquid entrained in a gas flowing at a selected rate through a nebulizer, comprising the steps of:
   (a) providing a nebulizer defining a gas flow path having a first axis;
   (b) providing in said gas flow path, means for forming a spray of liquid particles, said spray means being movable in said flow path relative to said first axis into preselected positions;

(c) providing a liquid supply means in flow communication with said spray means, said liquid supply means supplying said spray means with a liquid;

(d) generating a spray of liquid particles from said spray means and dispersing said particles in said flow path;

(e) flowing said gas at a selected rate along said flow path in said nebulizer so as to entrain said liquid particles therein; and (f) moving said spray means relative to said first axis to regulate the amount of liquid entrained by said flowing gas.

* * * * *